US012137951B2

United States Patent
Daniel et al.

(10) Patent No.: US 12,137,951 B2
(45) Date of Patent: Nov. 12, 2024

(54) BONE PLATES HAVING POLYGONAL LOCKING HOLES WITH THREAD INTERRUPTION, AND RELATED SYSTEMS AND METHODS

(71) Applicant: DePuy Synthes Products, Inc., Raynham, MA (US)

(72) Inventors: Steffan Daniel, Solothurn (CH); Andreas Baeriswyl, Büren an der Aare (CH); Sol Posada, Zuchwil (CH); Joel Oberli, Niederdorf (CH); Mirko Rocci, Bettlach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 450 days.

(21) Appl. No.: 17/345,152

(22) Filed: Jun. 11, 2021

(65) Prior Publication Data
US 2022/0395306 A1    Dec. 15, 2022

(51) Int. Cl.
*A61B 17/80* (2006.01)
*A61B 17/86* (2006.01)
*A61B 17/90* (2006.01)

(52) U.S. Cl.
CPC ...... *A61B 17/8057* (2013.01); *A61B 17/8014* (2013.01); *A61B 17/8047* (2013.01); *A61B 17/8052* (2013.01); *A61B 17/8605* (2013.01); *A61B 17/90* (2021.08)

(58) Field of Classification Search
CPC ............ A61B 17/8057; A61B 17/8014; A61B 17/8061; A61B 17/8605; A61B 17/866; A61B 17/90; A61B 17/80; A61B 17/8047; A61B 17/8052; A61B 17/808; A61B 2017/00862
USPC ........ 606/291, 280, 286, 289, 298, 305, 315
See application file for complete search history.

(56) References Cited

U.S. PATENT DOCUMENTS

| | | | |
|---|---|---|---|
| 7,303,564 B2 | 12/2007 | Freid et al. | |
| 10,772,665 B2 | 9/2020 | Bosshard et al. | |
| 2006/0235400 A1* | 10/2006 | Schneider | A61B 17/8052 606/291 |
| 2010/0312286 A1* | 12/2010 | Dell'Oca | A61B 17/8057 606/291 |
| 2016/0192968 A1* | 7/2016 | Chan | A61B 17/1782 470/10 |
| 2018/0064476 A1* | 3/2018 | Lopez | A61B 17/8014 |
| 2019/0328430 A1 | 10/2019 | Bosshard et al. | |

(Continued)

*Primary Examiner* — Marcela I. Shirsat
(74) *Attorney, Agent, or Firm* — BakerHostetler

(57) ABSTRACT

A bone plate defines an interior surface that defines: a hole extending through the plate along an axis; plate threads configured for locking with a threaded head of a locking screw; first, second, and third columns sequentially located about the axis; a first corner extending tangentially from the second to the first column; and a second corner extending tangentially from the third to the first column. The first and second corners are substantially equidistantly spaced from the axis. The plate threads extend across the first, second, and third columns and the first and second corners. The interior surface defines a recess between the second and third columns and facing the first column. An apex of the recess is spaced further from the axis than are the first and second corners, such that the recess circumferentially interrupts at least a portion of at least one of the plate threads.

21 Claims, 7 Drawing Sheets

(56) References Cited

U.S. PATENT DOCUMENTS

2020/0390483 A1  12/2020  Oberli et al.
2021/0015526 A1* 1/2021  Oberli ............... A61B 17/8014

* cited by examiner

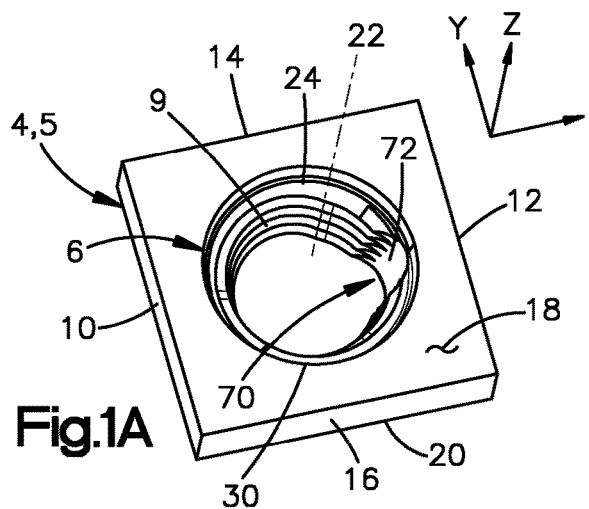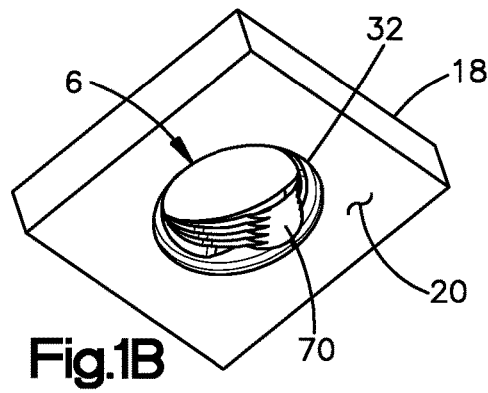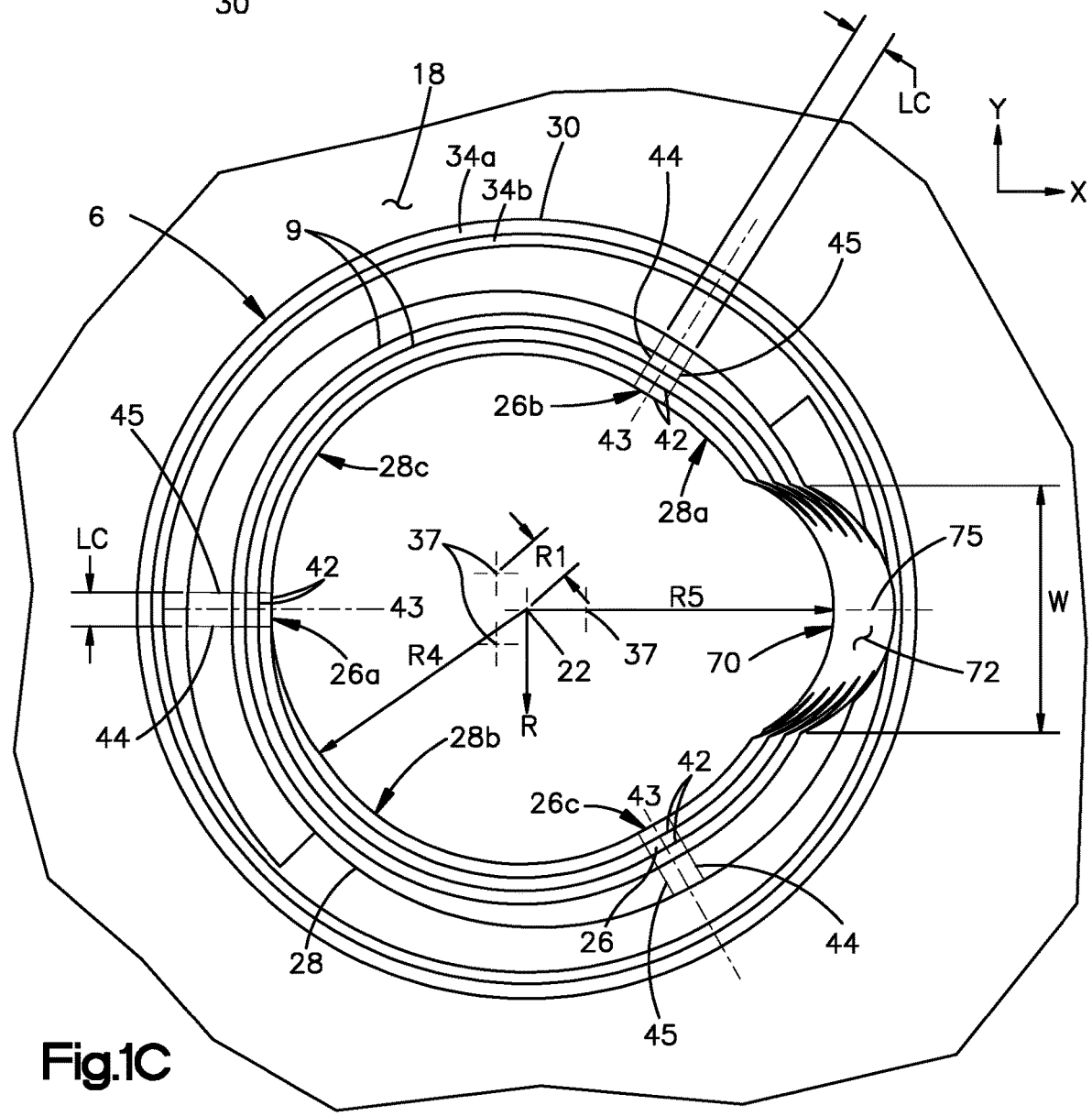

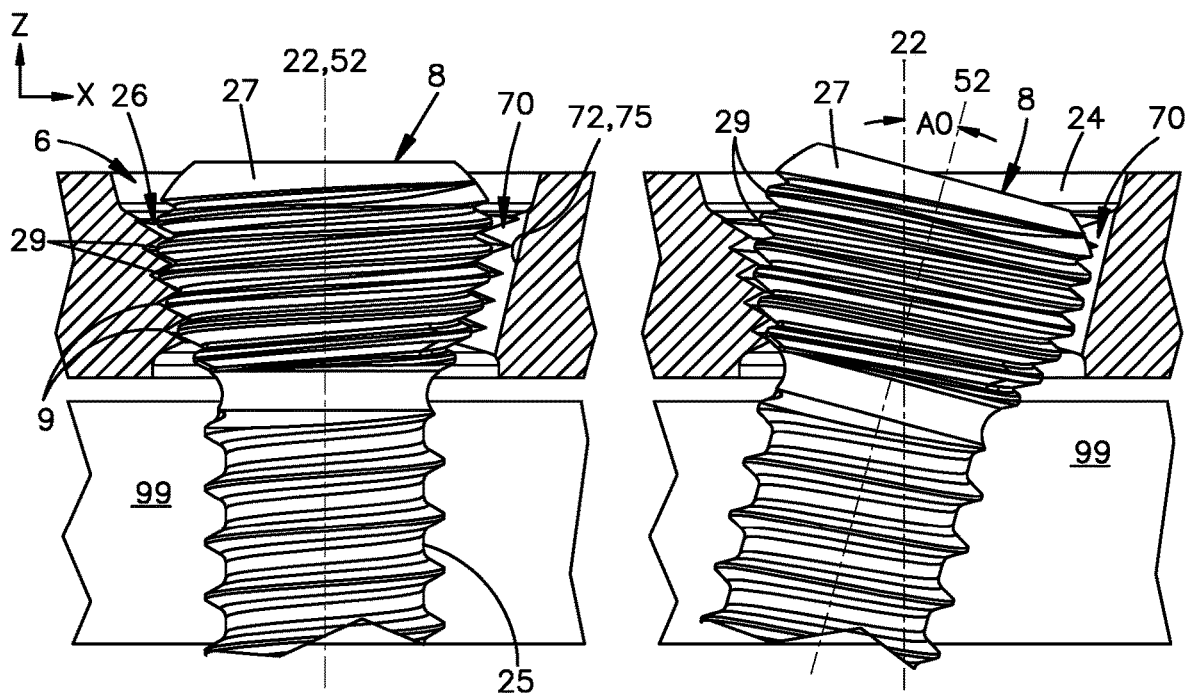
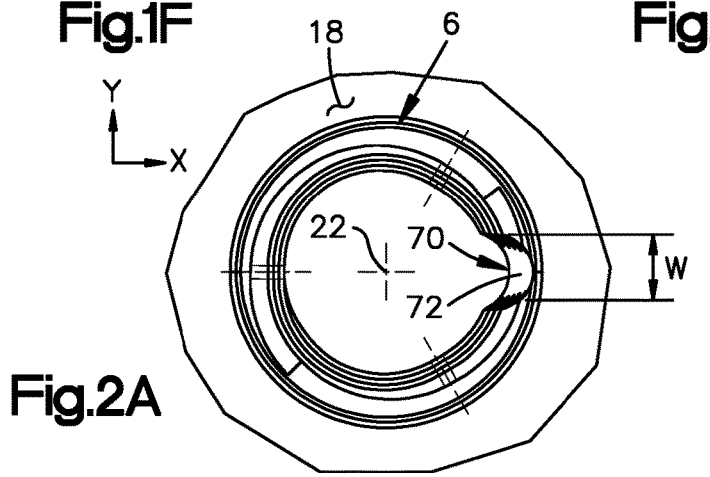
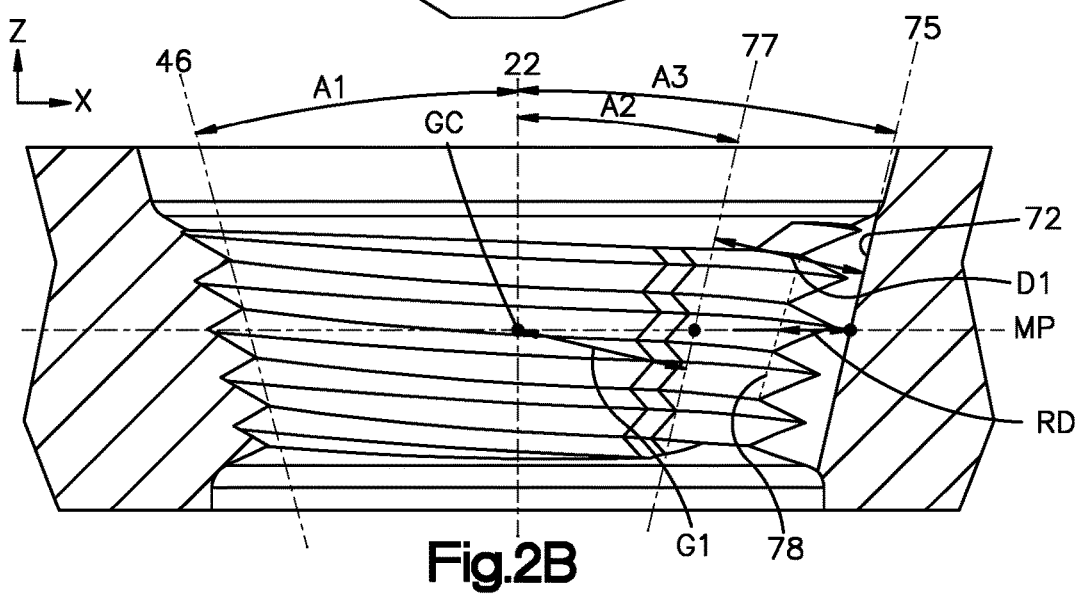

BONE PLATES HAVING POLYGONAL LOCKING HOLES WITH THREAD INTERRUPTION, AND RELATED SYSTEMS AND METHODS

TECHNICAL FIELD

The present invention relates to bone plates for receiving bone anchors to affix the bone plates to bone, and particularly relates to bone plates having threaded fixation holes that include a thread interruption.

BACKGROUND

Bone plate systems for the internal fixation of bone fractures are well known. Conventional bone plate systems are particularly well-suited to promote the healing of a fracture. A bone anchor, such as a bone screw, is inserted through a fixation aperture or hole in a bone plate and is threaded into bone to compress, neutralize, buttress, tension, band, and/or bridge the fracture ends together. Bone screws that are capable of locking with the bone plate can be employed to transfer loads from one fractured bone part, over a plate, and onto another fractured bone part without drawing the bone against the plate, and to avoid loosening or backing out the bone screws with respect to the plate (which can lead to poor alignment and poor clinical results). One known embodiment of such a screw employs a screw head with external threads for engaging with a corresponding thread on the inner surface of a fixation hole, which are hereinafter referred to as "locking holes", to lock the screw to the plate. These screws, which are hereinafter referred to as "locking screws", can include standard-type locking screws that are configured to lock within a fixation hole substantially only at a "nominal" orientation whereby the central screw axis is substantially aligned with the central hole axis, as well as "variable-angle" (VA) locking screws that are configured to lock within a fixation hole at either a nominal orientation or an "angulated" orientation whereby the central screw axis is oriented at an acute angle with respect to the respective central hole axis.

Bone plate systems can also be adapted to provide anatomical reduction between fractured bone parts. The bone plates of such systems include one or more holes having ramp geometries that engage a smooth exterior surface of a screw head of a "compression screw" in a manner causing dynamic compression, meaning that the bone plate translates with respect to the compression screw and underlying bone along a direction generally perpendicular to the screw axis of the compression screw. Such holes are hereinafter referred to as "compression holes". Bone plates can include both locking holes and compression holes. For example, one or more of the locking holes can be employed to receive a locking screw that affixes the bone plate to a first underlying bone segment. One or more of the compression holes can then be employed to receive a compression screw that drives into a second underlying bone segment and effectively pushes, via engagement between the head of the compression screw and the ramp geometry within the hole, the bone plate in a translation direction that reduces a gap between the first and second underlying bone segments.

SUMMARY

According to an embodiment of the present disclosure, a bone plate has an outer surface, a bone-facing surface opposite the outer surface, and an interior surface that defines at least one hole extending from the outer surface to the bone-facing surface along a central hole axis. The interior surface further defines plate threads that extend between the outer and bone-facing surfaces and are configured for locking engagement with external threads on a head of a locking bone screw; first, second, and third columns sequentially located about the central hole axis; a first corner extending tangentially from a first side of the second column to a second side of the first column; and a second corner extending tangentially from a second side of the third column to a first side of the first column. The first and second corners are substantially equidistantly spaced from the central hole axis at a first distance measured along a radial direction perpendicular to the central hole axis. The plate threads extend across the first, second, and third columns and across the first and second corners. The interior surface further defines a recess located between the second and third columns and facing the first column. An apex of the recess is spaced from the central hole axis at a second distance that is greater than the first distance, such that the recess circumferentially interrupts at least a portion of a thread-form of at least one of the plate threads.

According to another embodiment of the present disclosure, a bone fixation system includes a bone plate having an outer surface, a bone-facing surface opposite the outer surface, and an interior an interior surface that defines at least one hole that extends from the outer to the bone-facing surface along a central hole axis. The interior surface further defines plate threads that extend between the outer and bone-facing surfaces; first, second, and third columns sequentially located about the central hole axis; a first corner extending tangentially from a first side of the second column to a second side of the first column; and a second corner extending tangentially from a second side of the third column to a first side of the first column. The first and second corners are substantially equidistantly spaced from the central hole axis at a first distance measured along a radial direction perpendicular to the central hole axis. The plate threads extend across the first, second, and third columns and across the first and second corners. The interior surface further defines a recess located between the second and third columns and facing the first column. An apex of the recess is spaced from the central hole axis at a second distance that is greater than the first distance, such that the recess circumferentially interrupts at least a portion of a thread-form of at least one of the plate threads. The bone fixation system includes a bone screw having a head and a shaft that extends from the head in a distal direction. The shaft has external threads configured to engage underlying bone, and the head is configured to engage any of the first, second, and third columns in a manner affixing the bone plate to the underlying bone.

According to an additional embodiment of the present disclosure, a bone fixation system includes a bone plate having an outer surface, a bone-facing surface opposite the outer surface, and an interior an interior surface that defines at least one hole that extends from the outer to the bone-facing surface along a central hole axis. The interior surface further defines plate threads that extend between the outer and bone-facing surfaces; first, second, and third columns sequentially located about the central hole axis; a first corner extending tangentially from a first side of the second column to a second side of the first column; and a second corner extending tangentially from a second side of the third column to a first side of the first column. The first and second corners are substantially equidistantly spaced from the central hole axis at a first distance measured along a radial direction perpendicular to the central hole axis. The plate threads extend across the first, second, and third columns and across the first and second corners. The interior surface further defines a recess located between the second and third columns and facing the first column. An apex of the recess is spaced from the central hole axis at a second distance that is greater than the first distance, such that the recess circumferentially interrupts at least a portion of a thread-form of at least one of the plate threads. The bone fixation system includes an instrument having a distal mounting portion that includes a first formation configured to mate with the hole and a protrusion extending outwardly from the first formation. The protrusion and the recess define complimentary geometries, such that the protrusion is configured to mate with the recess in a manner securing the first formation with the hole.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings:

FIG. 1A is a top perspective view of a bone plate having a threaded locking hole that includes a recess, according to an embodiment of the present disclosure;

FIG. 1B is a top perspective view of the bone plate illustrated in FIG. 1A;

FIG. 1C is a top view of the bone plate illustrated in FIG. 1A;

FIG. 1F is a sectional side view of the hole illustrated in FIG. 1E with a head of a bone screw inserted therein at a nominal insertion angle;

FIG. 1G is a section side view of the hole illustrated in FIG. 1E with the head of the bone screw inserted therein at angulation;

FIG. 2A is a top view of a bone plate having a threaded locking hole that includes a recess, according to an embodiment of the present disclosure in which the recess has a width less than that of the hole shown in FIG. 1A;

FIG. 2B is a sectional side view of the hole taken along an apex of the recess illustrated in FIG. 2A;

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately", "about", and "substantially", as used herein with respect to dimensions, angles, ratios, and other geometries, takes into account manufacturing tolerances. Further, the terms "approximately", "about", and "substantially" can include 10% greater than or less than the stated dimension, ratio, or angle. Further, the terms "approximately", "about", and "substantially" can equally apply to the specific value stated.

As used herein, the term "dynamic compression" refers to an act of engaging a bone anchor against a bone plate in a manner causing the bone plate to translate relative to the bone anchor and underlying patient anatomy (e.g., underlying bone) along a direction that is generally perpendicular to an axis along which the bone anchor is inserted into underlying bone.

The embodiments disclosed herein pertain to bone plates having polygonal (e.g., trigonal) VA locking holes having an additional recess or "key-cut." As described below, the additional recess can be adapted for one or more various purposes, including: for mating with a complimentary formation of an instrument and/or tool for use with the bone plate; for providing adjacent portions of plate hole threads with enhanced deformation characteristics to improve locking engagement with a head of a locking screw; for providing extra space into which the screw head can angulate; and for increasing potential plate translation distance during dynamic compression, by way of non-limiting examples.

Figure 1D:
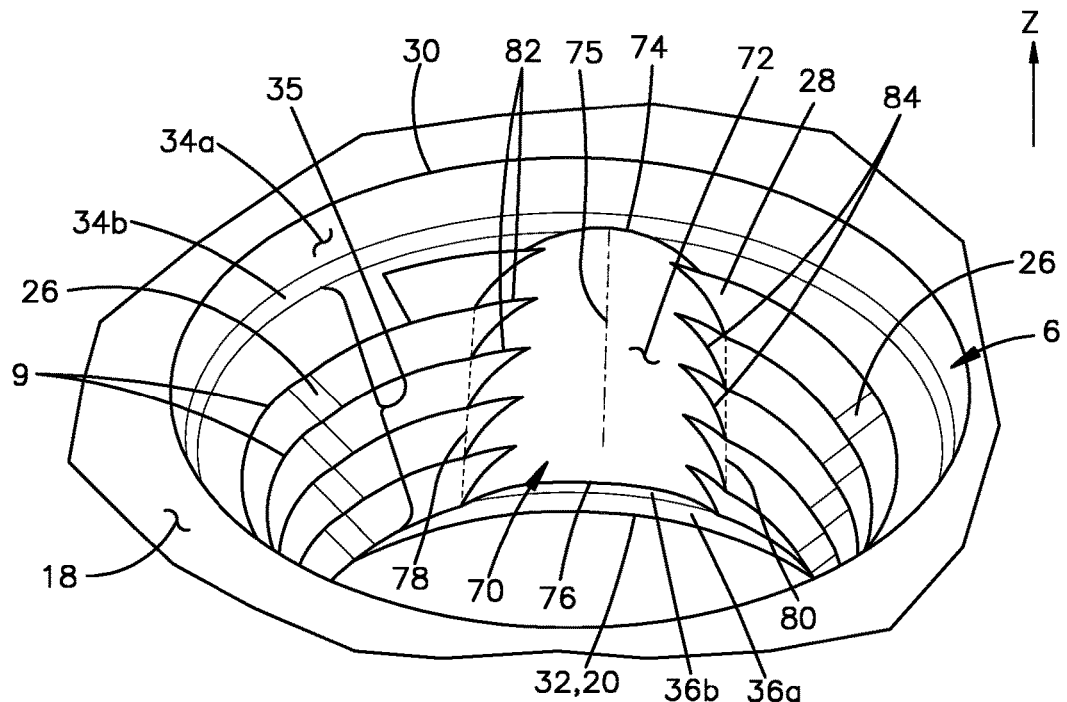
FIG. 1D is a top perspective view of the hole illustrated in FIG. 1A.

Referring now to FIGS. 1A-1G, according to an embodiment of the present disclosure, a bone plate 4 has a plate body 5 that defines therein a variable angle (VA) locking hole 6 that extends through the plate body 5. The plate body 5 defines an interior surface 24 that defines the hole 6. The interior surface 24 further defines one or more locking structures, such as internal threads 9, within the hole 6. The internal threads 9 can also be referred to as "plate threads" or "hole threads." The plate threads 9 extend along the interior surface 24 along one or more thread paths. The interior surface 24 also defines at least one recess 70 that interrupts at least some of the plate threads 9, as described in more detail below. The portion of the interior surface 24 within the recess 70 can be characterized as a "recess surface" 72. The recess 70 can also be referred to as a "key-cut." The hole 6 is configured for use with a complimentary locking bone anchor, such as a locking screw 8, which, as shown in FIGS. 1F-1G, can include a shaft 25 that advances through the hole 6 and into underlying bone 99 and a head 27 that affixes to the interior surface 24, as described in more detail below. Although the examples of bone anchors discussed below refer to bone screws, it should be appreciated that other types of bone anchors are within the scope of the present disclosure. Moreover, although the illustrated embodiments of the hole 6 show the hole 6 having a single recess 70, in other embodiments the hole 6 can include more than one recess 70.

As shown in FIGS. 1A-1B, the plate body 5 define a first end 10 and an opposed second end 12, which can be spaced from each other along a first or longitudinal direction X. The plate body 5 can also define a first lateral side 14 and an opposed second lateral side 16, which can be spaced from each other along a second or lateral direction Y. The longitudinal and lateral directions can be substantially perpendicular to each other. The bone plate 4 can also define an upper plate surface 18 (also referred to herein as an "outer surface" 18) configured to face away from the bone and an opposed lower plate surface 20 (also referred to herein as a "bone-facing surface") configured to face the bone. The upper and lower plate surfaces 18, 20 are spaced from each other along a third or vertical direction Z that is offset from the longitudinal and lateral directions X, Y. For example, longitudinal, lateral, and vertical directions X, Y, Z can be substantially perpendicular to each other. It is to be appreciated that, as used herein, the terms "longitudinal", "longitudinally", and derivatives thereof refer to the longitudinal direction X; the terms "lateral", "laterally", and derivatives thereof refer to the lateral direction Y; and the terms "vertical", "vertically", and derivatives thereof refer to the vertical direction Z. It should also be appreciated that a plane that contains the longitudinal and laterals directions X, Y can be referred to herein as a "horizontal" plane X-Y.

The hole 6 extends from the upper plate surface 18 to the lower plate surface 20 along a central hole axis 22. The central hole axis 22 is oriented along an axial hole direction. As used herein, the term "axial direction" (e.g., "axial hole direction" and "axial screw direction") is defined as the direction along which the respective axis extends. Furthermore, the directional terms "axial", "axially", and derivatives thereof refer to the respective axial direction. Thus, as used herein, the directional term "axially upward" and derivatives thereof refers to the axial hole direction from the lower plate surface 20 toward the upper plate surface 18. Conversely, the term "axially downward" and derivatives thereof refers to the axial hole direction from the upper plate surface 18 toward the lower plate surface 20. Thus, "axially upward" and "axially downward" are each mono-directional components of the "axial direction", which is bi-directional. In the embodiments depicted in the Figures, the axial hole direction (and thus also the central hole axis 22) is oriented along the vertical direction Z. Accordingly, the axial hole direction is also denoted by "Z" throughout this disclosure. It should be appreciated, however, that the scope of the present disclosure covers embodiments in which the axial hole direction (and thus also the central hole axis 22) is offset from the vertical direction Z at an oblique angle. It should also be appreciated that when the terms "axially upper", "axially lower," and the like are used with reference to a bone screw, such as a locking screw 8, such terms refer to a central axis 52 of the screw, particularly as the screw would be oriented within the hole 6 (see FIGS. 1F-1G).

The interior surface 24 extends axially downward from an upper perimeter 30 of the hole 6 located at an interface with the upper plate surface 18 (FIG. 1A). The interior surface 24 preferably includes one or more lead-in surfaces or chamfers that extend from the upper perimeter 30 axially downward into the hole 6. For example, as shown in FIGS. 1C-1D, the present embodiment includes a first lead-in surface 34a that is contiguous with the upper perimeter 30 and a second lead-in surface 34b extending axially downward from the first lead-in surface 34a. The lead-in surfaces 34a,b can extend a full revolution about the central hole axis 22, as shown, or can extend less than a full revolution about the central hole axis 22. The interior surface 24 also includes a primary or locking surface 35, into which the locking structures (e.g., plate threads 9) are formed. The interior surface 24 can also define one or more undercut surfaces (also referred to herein as a "relief surface") that extends axially upward from a lower perimeter 32 of the hole 6 which is located at an interface with the lower plate surface 20 (FIG. 1B). For example, the present embodiment includes a first undercut surface 36a that is contiguous with the lower perimeter 32 and a second undercut surface 36b extending axially upwards from the first undercut surface 36a toward the primary surface 35. The undercut surfaces 36a,b can extend a full revolution about the central hole axis 22, as shown, or can extend less than a full revolution about the central hole axis 22.

The locking structures of the hole 6 are configured to provide VA insertion of the locking screw 8 therein. For example, referring to FIG. 1C, the locking structures can include columns 26 that are sequentially located about a circumference of the interior surface 24. The interior surface 24 also defines a plurality of recesses 28 sequentially located circumferentially between the columns 26. Stated differently, the columns 26 and recesses 28 are alternately disposed along a circumference of the interior surface 24. The recesses 28 are also referred to herein as "corner rounds" or "corners." The columns 26 and corners 28 extend axially between the upper and lower plate surfaces 18, 20. The columns 26 and corners 28 can be evenly spaced along the circumference of the hole 6. However, in other embodiments, the columns 26 and/or corners 28 can be un-evenly spaced about the circumference of the hole 6. Each of the corners 28 can define a central corner axis 37, each of which can be parallel with the central hole axis 22, although other orientations are possible for the central corner axes 37. Each central corner axis 37 can also be spaced from the central hole axis 22 by a distance R1, as measured along a radial direction R perpendicular to the central hole axis 22. The recess 70 is located within one of the corners 28. The recess 70 is preferably circumferentially centered at an apex of the respective corner 28, such that an apex trajectory 75 of the recess 70 is circumferentially spaced in equidistant fashion from the adjacent columns 26. In this manner, the recess 70 can be located directly opposite one of the non-adjacent columns 26, such as along the longitudinal direction X. However, in other embodiments the recess 70 need not be centered at the corner apex, and need not be located directly opposite a non-adjacent column 26.

Figure 1E:
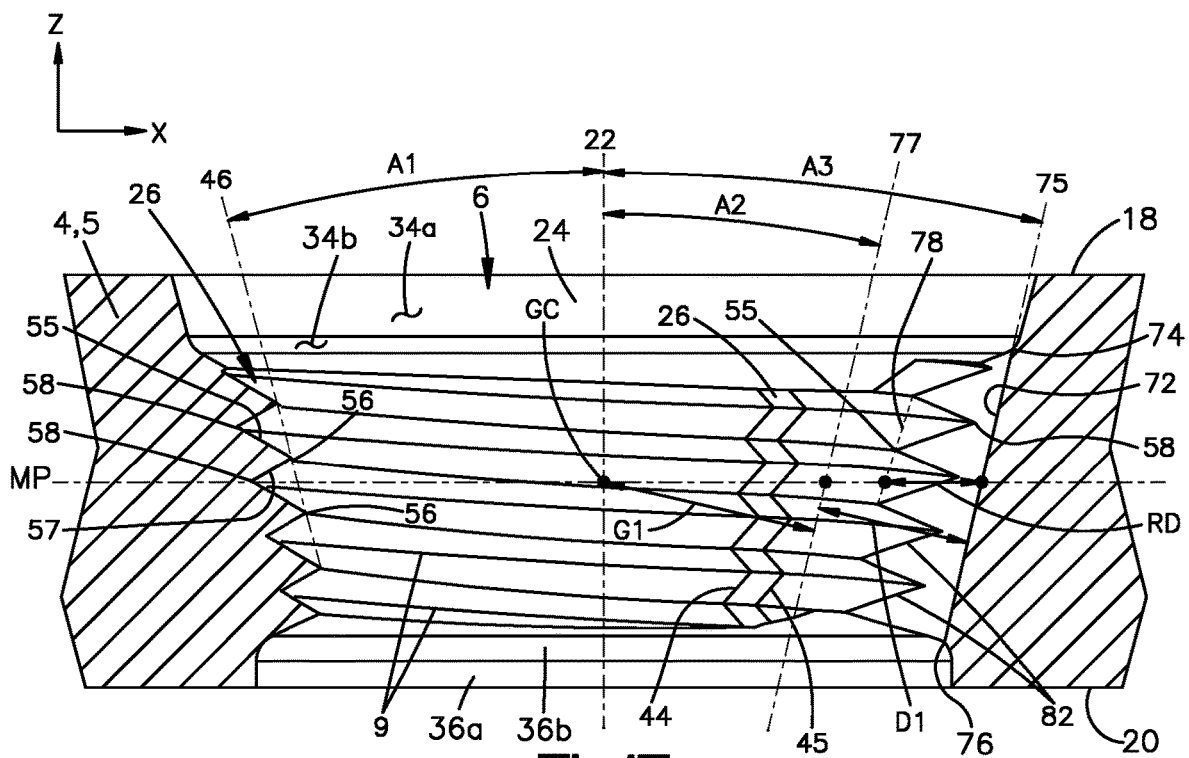
FIG. 1E is a sectional side view of the hole taken along an apex of the recess illustrated in FIG. 1C.

The plate threads 9 extend through the columns 26 and at least portions of the corners 28 along the one or more thread paths between the upper and lower plate surfaces 18, 20. Portions of the plate threads 9 that traverse a column 26 can be referred to herein as "column threads" 9. As shown in FIG. 1E, the plate threads 9 have a cross-sectional profile in the axial reference plane. Such as cross-sectional profile is also referred to as a "thread-form," and includes crests 56, roots 58, and upper and lower flanks 55, 57 that extend between the crests 56 and roots 58. As used herein with reference to the plate threads 9, the term "crest" refers to the apex of a fully-developed thread-form. The thread-forms of the plate threads 9 are configured for complimentary engagement (i.e., intermeshing) with exterior threads 29 on the head 27 of a locking screw 8, particularly for providing favorable mating engagement therebetween, including at various screw angulations, as described in more detail below.

As shown in FIG. 1C, each column 26 can define a first surface 42 substantially facing the central hole axis 22. The first surface 42 can also be referred to as a "radially innermost surface" of the column 26. Thus, the first surface 42 defines the crests 56 of the column threads 9. The first surface 42 of each column 26 extends between a first side 44 and a circumferentially opposed second side 45 of the column 26. The first and second sides 44, 45 of each column 26 can define interfaces between the column 26 and the circumferentially adjacent corners 28. The first surfaces 42 of the columns 26 can collectively define segments of a downward-tapering, generally frusto-conical shape, particularly one that defines a central cone axis coincident with the central hole axis 22.

The one or more thread paths can include a pair of non-intersecting thread paths (i.e., double-lead); however in other embodiments the one or more thread paths can include a single thread path (i.e., single-lead), or three or more thread paths (e.g., triple-lead, etc.). The thread paths are preferably helical, although other thread path types are within the scope of the present disclosure. As shown, the plate threads 9 preferably circumferentially traverse, in an uninterrupted fashion, each of the columns 26 and corners 28 outside the recess 70. The recess 70, however, circumferentially interrupts the plate threads 9. In particular, at least a portion of the recess surface 70 extends radially outward from the roots 58 of the plate threads 9. Stated differently, the plate threads 9 "bottom-out" within the recess 70. In other embodiments, portions of the corners 28 can also circumferentially interrupt the plate threads 9.

As shown in FIGS. 1F-1G, the columns 26 are configured such that, during insertion of a locking screw 8 within the hole 6, the screw shaft 25 of the locking screw 8 bypasses the columns 26, such that the interior surface 24 within the hole 6 engages the head 27 of the locking screw 8. After the screw shaft 25 bypasses the columns 26, the plate threads 9 in turn engage the external threads 29 on the head of the locking screw 8 in a manner providing locking engagement between the locking screw 8 and the bone plate 4. The structure and operation of the columns 26 is more fully described in U.S. Pat. No. 10,772,665, issued Sep. 15, 2020, in the name of Bosshard et al. ("the '665 Reference"); U.S. Patent Publication No. 2019/0328430 A1, published Oct. 31, 2019, in the name of Bosshard et al. ("the '430 Reference"); U.S. Patent 2020/0390483 A1, published Dec. 17, 2020, in the name of Oberli et al. ("the '483 Reference"); and U.S. Patent Publication No. 2021/0015526 A1, published Jan. 21, 2021, in the name of Oberli et al. ("the '526 Reference"), the entire disclosures of each of which are hereby incorporated by reference herein.

Referring again to FIG. 1C, the hole 6 defines a hole shape or "profile" in a horizontal reference plane X-Y. The hole 6 shape can thus be referred to as a "horizontal hole profile". It should be appreciated that the recess 70 deviates from the horizontal hole profile. Stated differently, the horizontal hole profile is defined irrespective of the recess 70. For example, during a manufacturing process of forming the hole 6 in the plate body 5, the hole 6 can be milled or otherwise cut into the plate body 5 so as to define the horizontal hole profile, and the recess 70 can be formed subsequently. The plate threads 9 can be formed within the hole 6 prior or subsequent to formation of the recess 70.

In the present embodiment, the hole 6 has a generally polygonal horizontal hole profile. In particular, the hole 6 of the present embodiment has a trigon (i.e., generally triangular) horizontal profile, although in other embodiments the hole 6 can have other types of polygonal horizontal profiles (e.g., rectangle, pentagon, hexagon, etc.), or can have a circular horizontal profile, as discussed in more detail below. The trigon-shaped hole 6 of the present embodiment has a first column 26a, a second column 26b, and a third column 26c located in a clockwise sequence along the circumference of the interior surface 24. The hole 6 also has a first corner 28a opposite the first column 26a, a second corner 28b opposite the second column 26b, and a third corner 28c opposite the third column 26c. The plate threads 9 preferably extend along respective thread paths that corresponds to the horizontal profile of the hole 6. Moreover, other features defined by the interior surface 24 can have a corresponding polygonal (e.g., trigon) horizontal profile, including the upper perimeter 30, the lead in surface(s) 34a,b, the one or more undercut surfaces 36a,b, and the lower perimeter 32. In this manner, the polygonal (e.g., trigon) horizontal hole profile can extend axially from the upper perimeter 30 to the lower perimeter 32 of the hole 6.

In the illustrated embodiment, the first surfaces 42 of the columns 26 have linear horizontal profiles. In other embodiments, one or more of the first surfaces 42 can have arcuate profiles having a relatively large radii (as measured from the central hole axis 22). Each column 26 can define a column centerline 43 that is spaced equidistantly between the first and second sides 44, 45 of the column 26. In a horizontal reference plane X-Y, the hole 6 can define a main radius R2 measured from the central hole axis 22 to the first surface 42 of the column 26 at the column centerline 43. It should be appreciated that various horizontal dimensions of the hole 6, including the main radius R2 and others, can be nominally measured along a horizontal midplane MP that is equidistantly located between the upper and lower plate surfaces 18, 20 (see FIG. 1E). Additionally, the location at which the central hole axis 22 intersects the horizontal midplane MP can define a geometric center GC of the hole 6, which also be employed for nominal dimensions of the hole 6.

With continued reference to FIG. 1C, in the present embodiment, the corners 28 extend tangentially from the first and second sides 44, 45 of the associated columns 26. In this manner, the first surfaces 42 of the columns 26 effectively define the "sides" of the trigon, while the corners 28 effectively define the corners of the trigon, each as viewed in the horizontal reference plane. Accordingly, the columns 26 of the present embodiment can also be referred to respectively as "sides" of the trigon-shaped hole 6. Each of the corners 28 can define a corner radius R3, measured from the corner axis 37. Each of the corners 28 is also positioned at a distance R4 from the central hole axis 22, measured along the radial direction R. Thus, the maximum of distance R4 is located at an apex of the corner 28. The recess 70 is positioned at a distance R5 from the central hole axis, measured along the radial direction R. Thus, the maximum of distance R5 is located at the apex trajectory 75 of the recess 70. The hole 6 is preferably configured such that, within any reference plane orthogonal to the central hole axis 22 axially located between the upper and lower ends 74, 76 of the recess surface 72, the maximum of distance R5 is greater than the maximum of distance R4. Stated differently, the recess 70 is located further from the central hole axis 22 than are the corners 28, along the radial direction R. The plate threads 9 extend along respective splines that revolve about the central hole axis 22 helically along the trigon profile of the interior surface 24 between the upper plate surface 18 and the lower plate surface 20. Additionally, the interior surface 24, including the columns 26 as well as the corners 28, tapers inwardly toward the central hole axis 22 from the upper plate surface 18 toward the lower plate surface 20. Moreover, as shown, outside the recess 70, the plate threads 9 can circumferentially traverse the columns 26 and the corners 28 in an uninterrupted fashion (i.e., the plate threads 9 need not bottom-out in the corners 28). Accordingly, outside the recess 70, the plate threads 9 can transition smoothly and continuously between the columns 26 and the corners 28.

The first surfaces 42 of each column 26 define a column length LC measured between the sides 44, 45 of the column 26. In the present embodiment, the column length LC can be substantially consistent within each column 26 as the thread path advances from the upper plate surface 18 toward the lower plate surface 20. In such embodiments, the column length LC can also be referred to as a "side length" LC of the trigon-shaped hole 6. The columns 26a-c of the present embodiment can have substantially equivalent column lengths LC, thus providing the hole 6 with a substantially equilateral triangular shape, as shown. In other embodiments, as described below, the column lengths LC of two or all of the columns can differ from one another. In further embodiments, the column length LC of one or more and up to all of the columns 26 can successively increase moving from the upper plate surface 18 toward the lower plate surface 20, thereby causing the corner radii R3 to progressively decrease toward the lower plate surface 20.

Referring now to FIG. 1D, the recess 70 extends axially between the upper and lower plate surfaces 18, 20. The recess surface 72 has a first or upper end 74 and a second or lower end 76 spaced from each other with respect to the vertical direction Z. The upper end 74 of the recess surface 72 can reside in a lead-in surface(s) 34a,b of the hole 6. In the present embodiment, the upper end 74 is located within the second lead-in surface 34b; although in other embodiments the upper end 74 can interface with the upper plate surface 18 (and thus define a portion of the upper perimeter 30 of the hole 6) or can reside in the first lead-in surface 34a or the primary surface 35. The lower end 76 of the recess surface 72 can reside in an undercut surface 36a,b of the hole 6. In the present embodiment, the lower end 76 is located within the second undercut surface 36b; although in other embodiments the lower end 76 can interface with the lower plate surface 20 (and thus define a portion of the lower perimeter 32 of the hole 6) or can reside in the first undercut surface 36a or the primary surface 35. It should be appreciated that the recess 70 can be located at a distinct axial portion of the hole 6. For example, in some embodiments, the recess 70 can reside entirely within an upper axial portion of the hole 6.

The recess surface 72 also extends horizontally from a first side 78 to a second side 80 about the circumference of the hole 6. As shown, the first and second sides 78, 80 of the recess surface 72 are remote from the circumferentially adjacent columns 26. In other embodiments, the first and second sides 78, 80 of the recess surface 72 can extend to, and share a common border with, the respective near sides 44, 45 of the circumferentially adjacent columns 26, preferably without extending into the columns 26. The recess 70 defines a recess width W, as measured between the first and second sides 78, 80 in a horizontal reference plane (FIG. 1C). The recess 70 also defines a radial recess depth RD, as measured from the first and second sides 78, 80 to the apex trajectory 75 along the radial direction R (FIG. 1E). It should be appreciated that the recess width W and depth RD can be measured at the horizontal midplane MP. The first and second sides 78, 80 of the recess surface 72 define respective thread interface boundaries 82, 84 with the thread-forms of the plate threads 9. In the embodiments illustrated herein, the plate threads 9 are fully circumferentially interrupted within the recess 70. Thus, the plate threads 9 bottom out along the recess surface 72, such that the roots 58 of the plate threads 9 respective circumferential termini 79 of the threads 9 along the thread interface boundaries 82, 84.

Referring again to FIG. 1E, in the axial reference plane, the crests 56 of the plate threads 9 extend along a crest trajectory axis 46. In the present embodiment, the crest trajectory axis 46 is linear, and can be oriented at an acute crest trajectory angle A1 relative to the central hole axis 22. The crest trajectory angle A1 can be in a range of about 5 degrees to about 30 degrees, and more particularly in a range of about 10 degrees to about 20 degrees, and preferably in a range of about 13 degrees to about 17 degrees. The crest trajectory angle A1 can be greater than an angle by which the first lead-in surface 34a descends into the hole 6 (as measured with respect to the central hole axis 22). The first lead-in surface 34a can have a linear profile in the reference plane, as shown; although in other embodiment the first lead-in surface 34a can have an arcuate profile in the reference plane. It should be appreciated that the second lead-in surface 34b can have a concave arcuate profile that provides a transition from the first lead-in surface 34a to the primary surface 35 of the hole 6. In other embodiments, the second lead-in surface 34b can have a linear profile in the axial reference plane.

The recess 70 extends along a central recess axis 77. In the present embodiment, the central recess axis 77 is angularly offset from the central hole axis 22 at an oblique recess axis angle A2. In other embodiments, the central recess axis 77 can be parallel with the central hole axis 22. As shown, the central recess axis 77 is spaced from the geometric center GC of the hole 6 by an axis separation distance G1, as measured along a direction perpendicular to the central recess axis 77. The recess surface 72 can have various three-dimensional (3D) geometries or "shapes," such as cylindrical, conical (e.g., frusto-conical), prism, or spherical, or segments thereof, by way of non-limiting examples. In the present embodiment, the recess surface 72 defines a segment of cylinder that has a central axis that is co-extensive with the central recess axis 77. Thus, in this embodiment, the recess apex trajectory 75 defines a recess taper angle A3, as measured from the central hole axis 22 to the apex trajectory 75, that is equivalent to the recess axis angle A2. Thus, the recess apex trajectory 75 is spaced from the central recess axis 77 by a distance D1, as measured along the direction perpendicular to the central recess axis 77. In the present embodiment, distance D1 is effectively the radius of the cylinder segment. In the present embodiment, the recess axis angle A2 and the recess taper angle A3 are slightly less than the crest trajectory angle A1, thus causing the radial recess depth RD to increase moving axially downward along the recess surface 70. The relative orientations of the crest trajectory axis 46 and the central recess axis 77, in combination with the cylindrical geometry of the recess surface 72, also causes the recess width W to increase, moving from the upper end 74 to the lower end 76 of the recess 70. The recess axis angle A2 and recess taper angle A3 can each be in a range from about 3 degrees to about 30 degrees, and more particularly in a range of about 7 degrees to about 20 degrees, and preferably in a range of about 11 degrees to about 15 degrees. In other embodiments, one or both of the recess axis angle A1 and the recess taper angle A3 can be substantially equivalent to the crest trajectory angle A1.

Referring now to FIGS. 1F-1G, threaded engagement between the plate threads 9 and external threads 29 on the head 27 of a VA locking screw 8 will be described. FIG. 1F shows the locking screw 8 inserted at a nominal orientation, i.e., when the screw 8 is inserted along a screw axis 52 that is substantially co-extensive with the central hole axis 22. FIG. 1G shows the locking screw 8 inserted at an angulated orientation, i.e., when the screw axis 52 is oriented at an acute angle A0 with respect to the central hole axis 22. Such angulated screw orientation can be referred to as "angulation." The columns 26 and corners 28 of the of the trigon-shaped hole 6 provide favorable threaded locking interface between the plate threads 9 and screw head threads 29, as more fully described in the '483 Reference. Moreover, the presence of the recess 70 provides additional benefits. For example, by interrupting the plate threads 9 in the foregoing manner, portions of the plate threads 9 along and adjacent the thread interface boundaries 82, 84 exhibit increased deformation during threaded engagement with the threads 29 of the head 27 of a VA locking screw 8. Such increases in the deformation of the plate threads 9 has been demonstrated to increase the threaded locking interface between the plate threads 9 and the threads 29 of the screw head 27, as more fully described in the '430 Reference. Furthermore, the presence of the recess 70 provides additional space into which the head 27 can angulate, as shown in FIG. 1G. It should also be appreciated that the recess taper angle A3 can maintain the recess apex in proximity to the screw head 27, thereby providing the foregoing benefits while also limiting any decrease in plate strength caused by the present of the recess 70.

Referring now to FIGS. 2A-2B, another embodiment of the VA locking hole 6 is shown, in which the recess 70 has a smaller recess width W than that of the embodiment shown in FIGS. 1A-1E. The hole 6 of this additional embodiment is otherwise similar to the hole 6 described above. Accordingly, like reference numbers from the embodiment described above will also be used in this additional embodiment. As with the hole 6 above, the recess surface 72 defines a segment of a cylinder that extends along the central recess axis 77, which is oriented at recess axis angle A2. In the present embodiment, distance D1 is less than that of the embodiment above, while the axis separation distance G1 is greater than that of the embodiment above, such that the recess apex trajectory 75 is spaced from the central hole axis at a radial distance substantially equivalent to the embodiment above. In additional embodiments, the geometry, dimensions, and spacing of the recess 70 can be varied as desired, including one or more and up all of the recess shape, recess width W, recess depth RD, recess axis angle A2, axis separation distance G1, recess taper angle A3, distance D1, while remaining within the scope of the present disclosure.

Figure 3A:
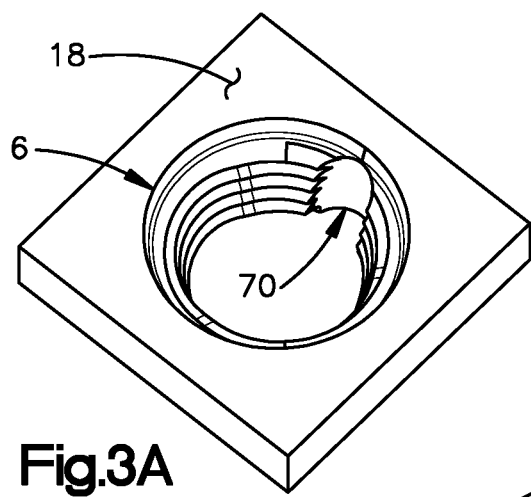
FIG. 3A is a top perspective view of a bone plate having a threaded locking hole that includes a recess, according to another embodiment of the present disclosure.
Figure 3B:
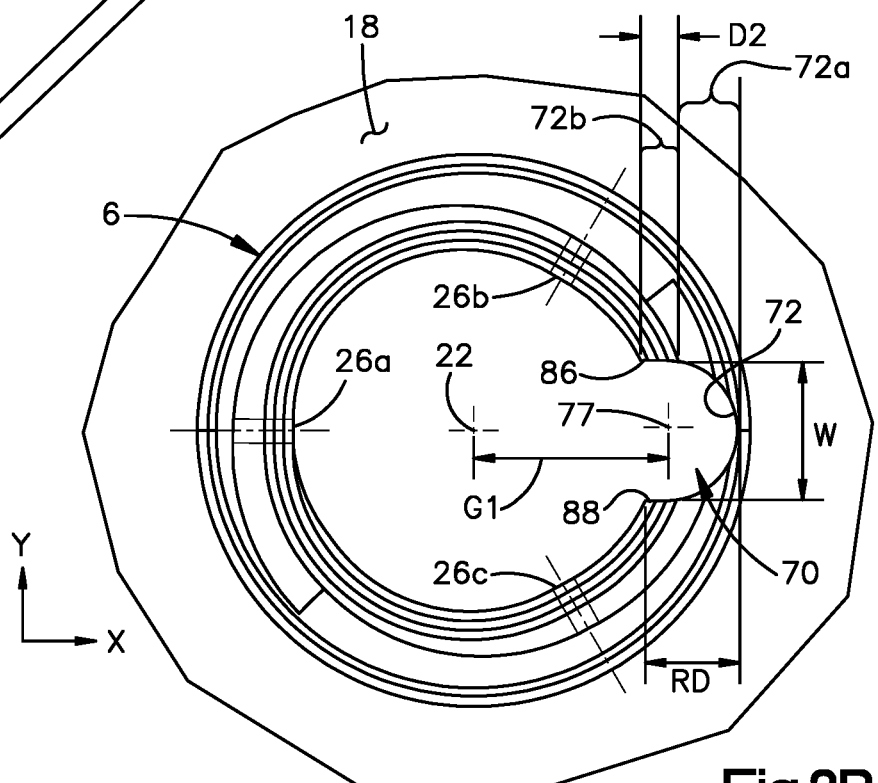
FIG. 3B is a top view of the bone plate illustrated in FIG. 3A.
Figure 3C:
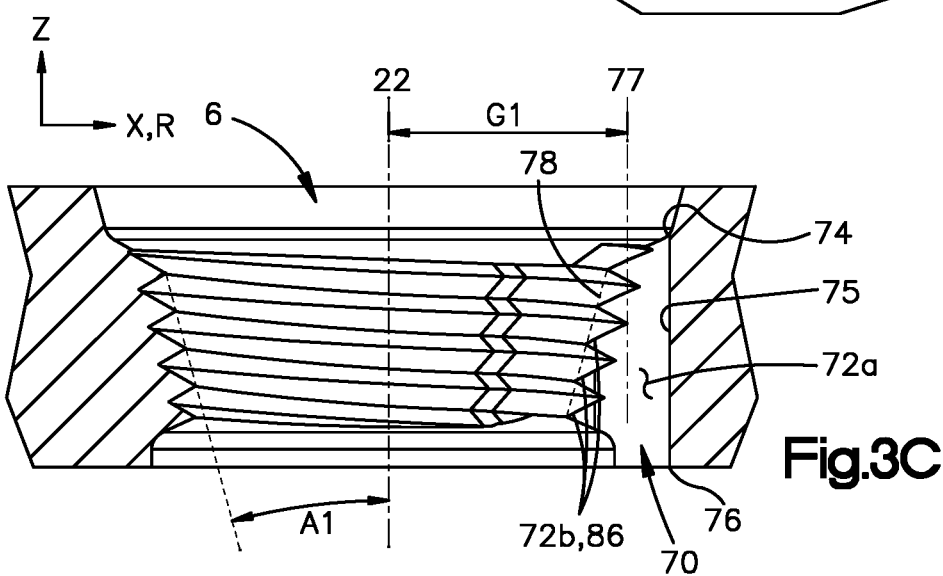
FIG. 3C is a sectional side view of the hole taken along an apex of the recess illustrated in FIG. 3B.

Referring now to FIGS. 3A-3C, an additional embodiment of the VA locking hole 6 is shown, in which the recess axis 77 is parallel with the central hole axis 22. Accordingly, in the present embodiment, the axis separation distance G1 is measured along the radial direction R. In such embodiments, and when the central hole axis 22 is oriented along the vertical direction Z, the recess apex trajectory 75 is also oriented along the vertical direction Z. The hole 6 of the present embodiment is otherwise generally similar to the holes 6 described above. Accordingly, like reference numbers from the embodiments described above will also be used in this additional embodiment. For the sake of brevity, the following disclosure will focus primarily on the differences between the VA locking hole 6 of the present embodiment and those of the embodiments above.

In the present embodiment, the recess surface 72 can include a primary portion 72a that defines a segment of a cylinder and includes the recess apex trajectory 75. The recess surface 72 further includes an extension portion 72b that extends from the primary portion 72a toward a central region of the hole 6, such as along the longitudinal direction X. The extension portion 72b can include opposed side surfaces 86, 88, which can extend parallel to each other, and which define portions of the respective sides 78, 80 of the recess surface 72. In other embodiments, the opposed side surfaces 86, 88 can extend at an angle with respect to each other. For example, the opposed side surfaces 86, 88 can taper away from each other toward the central region of the hole 6 or can taper toward each other toward the central region of the hole 6. Due to the crest trajectory angle A1, the extension portion 72b and opposed side surfaces 86, 88 thereof are predominantly located within a lower axial portion of the hole 6, as shown in FIG. 3C. In additional embodiments, the axis separation distance G1 can be increased along the longitudinal direction X, thereby also increasing the recess depth RD, and also increasing respective lengths D2 of the opposed side surfaces 86, 88 along the longitudinal direction X. It should be appreciated that distance G1 and the recess depth RD can be increased as needed. For example, in further embodiments, one or both of the axis separation distance G1 and the recess depth RD can extend radially beyond the upper perimeter 30 of the hole 6 (or at least beyond the portion of the upper perimeter 30 that is remote from the recess 70).

Figure 4A:
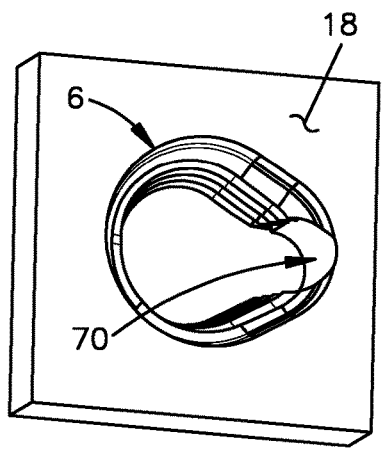
FIG. 4A is a top perspective view of a bone plate having a threaded locking hole that includes an elongated recess, according to another embodiment of the present disclosure.
Figure 4B:
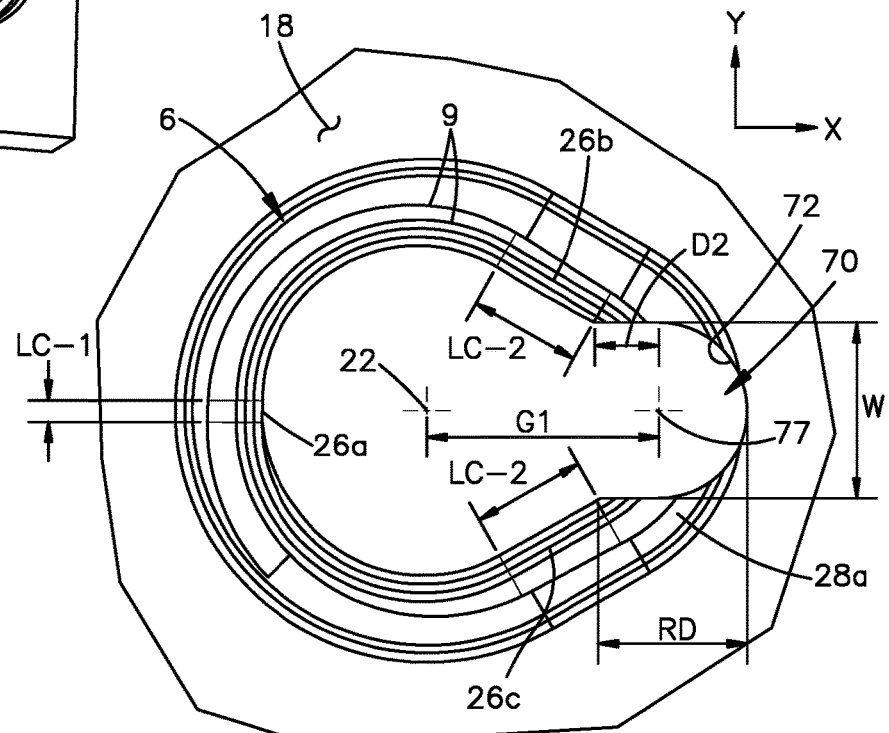
FIG. 4B is a top view of the bone plate illustrated in FIG. 4A.
Figure 4C:
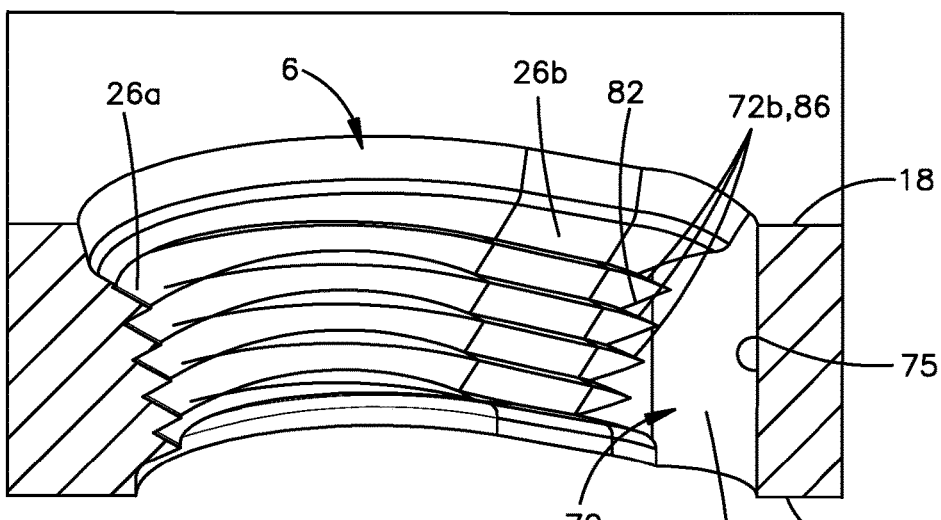
FIG. 4C is a sectional perspective view of the hole taken along an apex of the elongated recess illustrated in FIG. 4B.

Referring now to FIGS. 4A-4C, a further embodiment of the VA locking hole 6 is shown, in which the column lengths LC-2 of the second and third columns 26b,c (i.e., the two columns 26b,c adjacent the recess 70) are greater than the column length LC-1 of the first column 26a (i.e., the column 26a opposite the recess 70). Thus, the second and third columns 26b,c can be characterized as being elongated relative to the first column 26a. Additionally, the recess width W and recess depth RD are greater than those of the embodiment shown in FIGS. 3A-3C. The hole 6 of the present embodiment is otherwise generally similar to the holes 6 described above with reference to FIGS. 3A-3C. Accordingly, like reference numbers from the embodiments described above will also be used in this additional embodiment. For the sake of brevity, the following disclosure will focus primarily on the differences between the VA locking hole 6 of the present embodiment and those of the embodiments above.

The increased recess depth RD can be at least partially provided by increasing the axis separation distance G1 and/or the lengths D2 of the opposed side surfaces 86, 88 relative to the embodiment shown in FIGS. 3A-3C. The increased lengths D2 of the side surfaces 86, 88 can provide the recess 70 with a more slot-like geometry. In the present embodiment, the recess surface 72, including the apex trajectory 75 thereof, can extend entirely from the upper plate surface 18 to the lower plate surface. Additionally, the elongated second and third columns 26*b,c* effectively provide yet additional space to receive the head of the bone screw 8 when the bone screw 8 is inserted at a high angulation A0 that causes the head 27 to enter the first corner 28*a* and/or the recess 70. Additionally, the plate threads 9 along the second and third elongated columns 26*b,c*, the first corner 28*a*, and the thread interface boundaries 82, 84 can provide increased locking thread interface between the plate threads 9 and screw head threads 29 at such angulations A0. Moreover, the opposed side surfaces 86, 88 can also be characterized as relief surfaces for avoiding, minimizing, or at least reducing contact between abrupt and/or sharp edges of the plate threads 9 and screw head threads 29 at the high angulations discussed above. In this manner, the elongated second and third columns 26*b,c* and the side surfaces 86, 88 of the recess 70 can provide benefits similar to those more fully described with reference to FIGS. 12A-13H of the '526 Reference.

It should be appreciated that the recesses 70 of the VA locking holes 6 according to the embodiments described above can provide yet additional benefits. For example, the recesses 70 can be configured to receive and mate with a complimentary structure of an instrument or tool, such as a drill guide and/or a bending pin, by way of non-limiting examples. Additionally or alternatively, the recesses 70, particularly those shown in FIGS. 3A-4C, can be employed to receive a guide member, such as a Kirschner wire ("K-wire"), before, during, or after insertion of a bone screw within the hole 6.

Figure 5A:
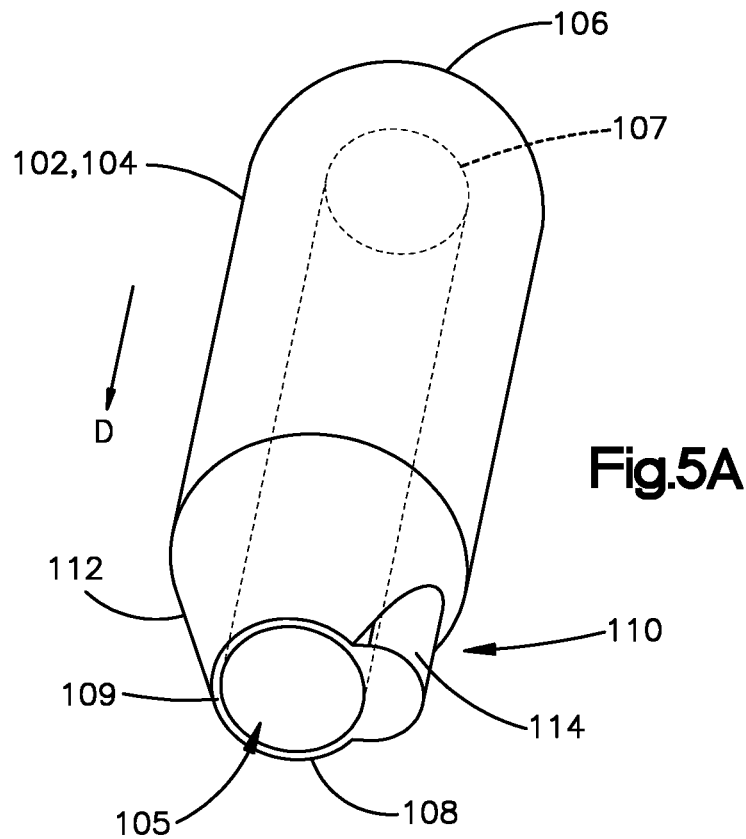
FIG. 5A is a perspective view of a drill guide configured for use with threaded locking holes similar to those illustrated in FIGS. 1A-4C, according to a further embodiment of the present disclosure.
Figure 5B:
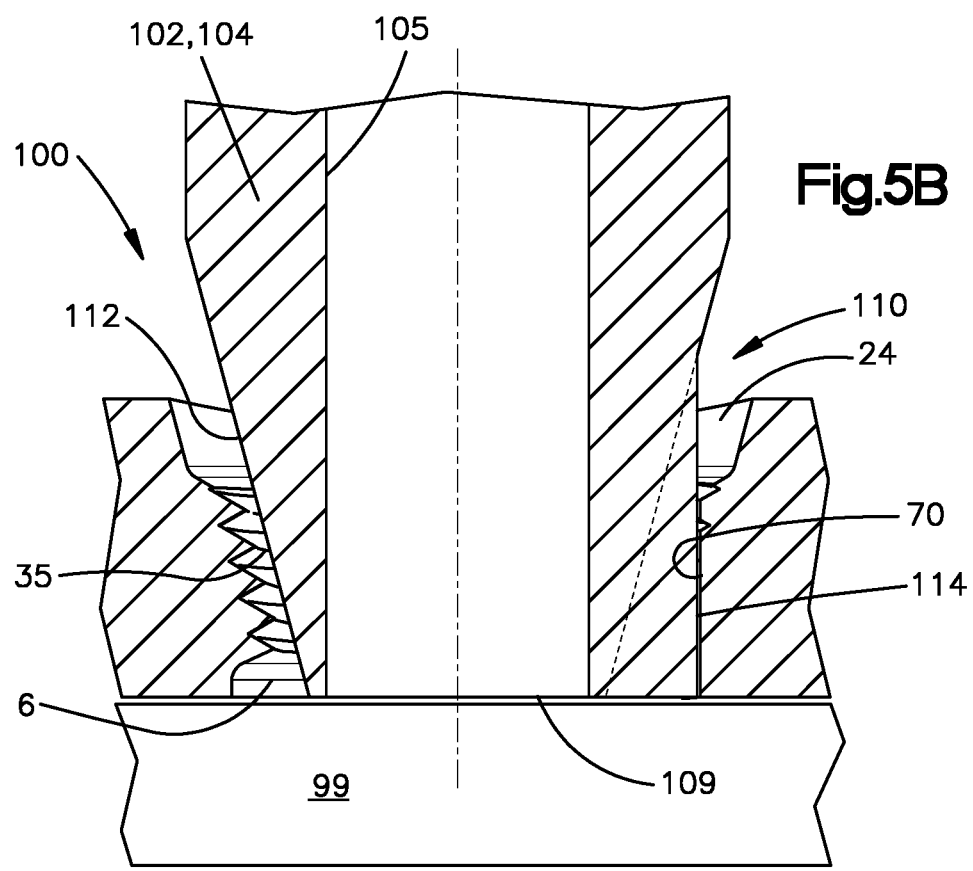
FIG. 5B is a sectional side view of a portion of the drill guide illustrated in FIG. 5A, shown seated in a hole.

Referring now to FIGS. 5A-5B, a VA locking hole 6 of the present disclosure can be configured to mate with an instrument, such as a drill guide 102. The bone plate 4 and drill guide 102 can together define a bone fixation system 100. The drill guide 102 includes a guide body 104 that extends from a proximal end 106 to a distal end 108 along a distal direction D. The guide body defines a channel 105 that extends from the proximal channel opening 107 at the proximal end 106 to a distal channel opening 109 at the distal end 108. The guide body 104 defines a distal mounting formation 110 that can be configured to extend within the hole 6 and seat against the interior surface 24 thereof. The distal mounting formation 110 can include an exterior primary mounting surface 112 having a frusto-conical shape configured to mate with the primary surface 35 of the hole 6 such that the distal channel opening 109 is open to underlying bone 99. The distal mounting formation 110 can also include a protrusion 114 that extends away from the primary mounting surface 112 and has a geometry complimentary with that of the recess 70. Accordingly, as shown in FIG. 5B, the protrusion 114 can be configured to reside within and mate with the recess 70 of the hole 6 in a manner securing the drill guide 102 in a desired orientation relative to the hole 6 for targeting the underlying bone 99.

Figure 6A:
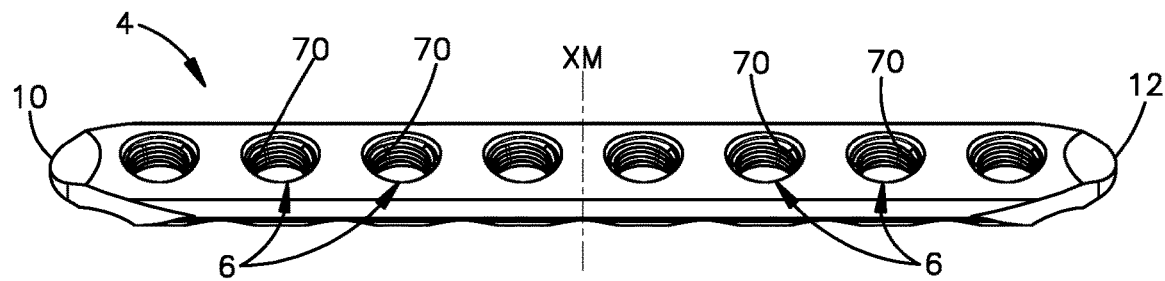
FIG. 6A is a top perspective view of a bone plate having multiple threaded locking holes configured similarly to those illustrated in FIGS. 1A-4C, according to yet another embodiment of the present disclosure.
Figure 6B:
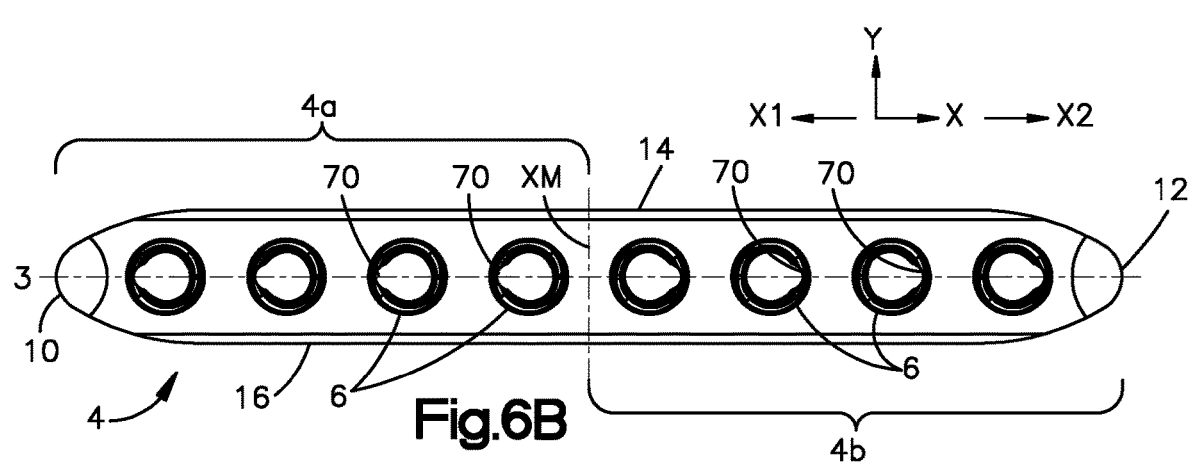
FIG. 6B is a top view of the bone plate illustrated in FIG. 6A.

Referring now to FIGS. 6A-6B, an example embodiment of a bone plate 4 is shown having a plurality of VA locking holes 6 each having a recess 70, as described above. In this embodiment, the holes 6 are arranged to provide the bone plate 4 with the selective dynamic compression along opposed first and second longitudinal directions X1, X2. The plate 4 has a first end 10 and a second end 12 spaced from each other along a longitudinal axis 3 oriented along the longitudinal direction X. The first longitudinal direction X1 extends from the second end 12 to the first end 10. The second longitudinal direction X2 extends from the first end 10 to the second end 12. The holes 6 can be arranged in a first group of holes 6 along a first longitudinal region 4*a* of the plate 4 and a second group of holes 6 along a second longitudinal region 4*b* of the plate 4. In this example, the first and second longitudinal regions 4*a*, 4*b* extend to a common boundary at a longitudinal midpoint XM of the plate 4. Each hole 6 of the first group is oriented to provide dynamic compression (i.e., to translate the plate 4 relative to underlying bone 99) in the first longitudinal direction X1. Each hole 6 of the second group is oriented to provide dynamic compression in the second longitudinal direction X2. It should be appreciated that the arrangement and orientation of the holes 6 can be adapted as needed to provide the plate 4 with dynamic compression capabilities in various directions according to the needs of a particular surgical treatment.

Figure 6C:
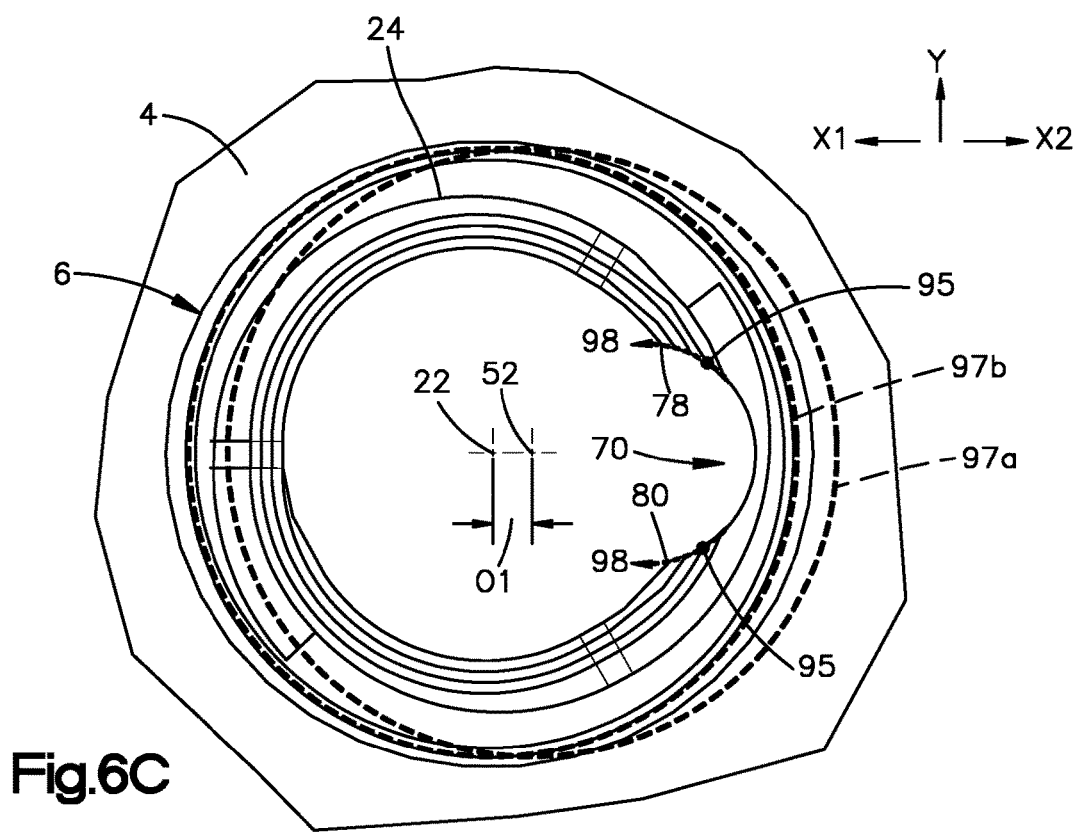
FIG. 6C is an enlarged top view of one of the holes illustrated in FIG. 6B.

Referring now to FIG. 6C, each hole 6 and its associated recess 70 can be configured to provide dynamic compression responsive to eccentric insertion of a bone screw, particularly a compression screw. During eccentric insertion, the compression screw is inserted along an insertion axis 52 that is offset from the central hole axis 22 at an offset distance O1 along on offset direction, which in this example is the second longitudinal direction X2. During such eccentric screw insertion, the recess 70 provides, among other things, additional radial space that can allow the external threads on the screw shaft to advance through the hole 6 without mechanical interference against the interior surface 24 of the hole 6. In this manner, the recess 70 can increase the translation distance provided by the hole 6, thus improving the translation capabilities of the bone plate 4 for dynamic compression. Additionally, the presence of the recess 70 can cause the eccentrically inserted screw head, denoted as 97*a*, to contact the interior surface 24 at contact locations 95 along the sides 78, 80 of the recess 70. Subsequent axial advancement of the head of the compression screw can cause the head to travel along contact paths 98 along the sides 78, 80 of the recess 70, which can effectively "funnel" or otherwise direct concurrent translation of the plate 4 relative to the screw along the second longitudinal direction X2, such as until the compression screw fully seats against the interior surface 24. At the full seated position of the compression screw head, denoted as 97*b*, the screw axis 55 can be substantially co-extensive with the central hole axis 22. Thus, in the illustrated example, the offset distance O1 also represents the translation distance of the plate 4 caused by the dynamic compression. Moreover, referring again to FIG. 6B, the orientation of each hole 6, particularly the respective position of the recess 70, can determine the translation direction provided by the hole 6. The bone plate 4 of the illustrated embodiment is configured to direct dynamic compression (i.e., plate translation) in either the first or second longitudinal direction X1, X2. It should be appreciated that in other embodiments, one or more of the holes 6 (and their recesses 70) can be oriented to provide dynamic compression along various directions offset from the first and second longitudinal directions X1, X2.

The plate body 5, locking screws 8, and compression screws described herein can each comprise one or more biocompatible materials. By way of non-limiting examples, the plate body 5 can be formed of a material selected from a group comprising: metal, such as titanium, titanium alloys (e.g., titanium-aluminum-niobium (TAN) alloys, such as Ti-6Al-7Nb, and titanium-aluminum-vanadium (TAV) alloys such as Ti-6Al-4V, titanium molybdenum alloys (Ti—Mo) or any other molybdenum metal alloy, and nickel-titanium alloys, such as nitinol), stainless steel, and cobalt base alloys (e.g., cobalt-chrome alloys); composite materials; polymeric materials; ceramic materials; and/or resorbable materials, including resorbable versions of the foregoing material categories (metals, composites, polymers, ceramics). Also by way of non-limiting examples, the locking screws 8 and compression screws can be formed of a material selected from a group comprising: metal, such as titanium, titanium alloys (e.g., TAN alloys, TAV alloys, such as Ti-6Al-4V, titanium molybdenum alloys (Ti—Mo) or any other molybdenum metal alloy, and nickel-titanium alloys, such as nitinol), stainless steel, cobalt base alloys (e.g., cobalt-chrome alloys); composite materials; polymeric materials; ceramic materials; and/or resorbable materials, including resorbable versions of the foregoing material categories (metals, composites, polymers, ceramics). Preferably, the material of the locking screws 8 and compression screws has a hardness that is greater than that of the material of the plate body 5. This parameter contributes to the threaded locking characteristics and the dynamic compression characteristics described throughout the present disclosure. Preferably, the plate body 5 primarily or entirely comprises titanium and the locking screws 8 and compression screws primarily or entirely comprise TAN. It should be appreciated, however, that other material compositions of the bone plates 4 and/or the screws are within the scope of the present disclosure.

Moreover, surfaces of the plate body 5 and/or the screws can optionally be subjected to one or more processes, such as coating, treating, and/or finishing processes, which can be performed to provide such surfaces, or the underlying subject body material, with certain characteristics, such as to adjust hardness, softness, and/or friction parameters of the body material, as more fully described in the '483 and '526 References.

It should be appreciated that the various hole 6 parameters described above are provided as exemplary features for adapting the holes 6 to achieve selective locking engagement or dynamic compression with the heads of respective locking screws or compression screws. These parameters can be adjusted as needed without departing from the scope of the present disclosure.

It should also be appreciated that in additional embodiments, the interior surface 24 of any hole 6 can be defined by an insert plate body (e.g., an "insert" or "inlay") that is fitted within an axial aperture or receptacle of the plate body 5. In such embodiments, the bone plate 4 can be provided in a kit that includes a plurality of interchangeable inserts having different hole 6 shapes and geometries, such that the physician can select the particular insert that provides the desired characteristics needed.

It should further be appreciated when a numerical preposition (e.g., "first", "second", "third") is used herein with reference to an element, component, dimension, or a feature thereof (e.g., "first" column, "second" recess, "second" end, "first" direction), such numerical preposition is used to distinguish said element, component, dimension, and/or feature from another such element, component, dimension and/or feature, and is not to be limited to the specific numerical preposition used in that instance. For example, a "first" column, recess, end, or direction, by way of non-limiting examples, can also be referred to as a "second" column, recess, end, or direction in a different context without departing from the scope of the present disclosure, so long as said elements, components, dimensions and/or features remain properly distinguished in the context in which the numerical prepositions are used.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. In particular, one or more of the features from the foregoing embodiments can be employed in other embodiments herein. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone plate, comprising:
an outer surface and a bone-facing surface opposite the outer surface; and
an interior surface that defines at least one hole that extends from the outer surface to the bone-facing surface along a central hole axis, wherein the interior surface further defines:
plate threads extending between the outer surface and the bone-facing surface, wherein the plate threads are configured for locking engagement with external threads on a head of a locking bone screw;
first, second, and third columns sequentially located about the central hole axis;
a first corner extending tangentially from a first side of the second column to a second side of the first column;
a second corner extending tangentially from a second side of the third column to a first side of the first column, wherein the first corner and the second corner are substantially equidistantly spaced from the central hole axis at a first distance measured along a radial direction perpendicular to the central hole axis, and the plate threads extend across the first, second, and third columns and across the first corner and the second corner; and
a recess located between the second and third columns and facing the first column, wherein an apex of the recess is spaced from the central hole axis at a second distance that is greater than the first distance, such that the recess circumferentially interrupts at least a portion of a thread-form of at least one of the plate threads.

2. The bone plate of claim 1, wherein the apex of the recess extends along an apex trajectory that tapers inwardly toward the central hole axis from the outer surface toward the bone-facing surface at an acute angle.

3. The bone plate of claim 2, wherein the acute angle of the apex trajectory axis is in a range from about 11 degrees to about 15 degrees.

4. The bone plate of claim 3, wherein each of the first, second, and third columns defines a respective crest trajectory axis that intersects crests of the plate threads, wherein each crest trajectory axis tapers inwardly toward the central hole axis from the outer surface toward the bone-facing surface at an acute angle, wherein:
the acute angles of the crest trajectory axes are substantially equivalent, and
the acute angle of the apex trajectory is less than the acute angle of the crest trajectory axes.

5. The bone plate of claim 2, wherein the interior surface includes:
a primary axial portion along which the plate threads extend, one or more lead-in surfaces that extend between the outer surface and the primary axial portion, and one or more undercut surfaces that extend between the primary axial portion and the bone-facing surface,
wherein the recess extends from a first end that interfaces with the one or more lead-in surfaces and a second end that interfaces with the one or more undercut surfaces.

6. The bone plate of claim 1, wherein the apex of the recess extends along an apex trajectory that is substantially parallel with the central hole axis.

7. The bone plate of claim 6, wherein the apex of the recess extends from, and is contiguous with, the outer plate surface and the bone-facing surface.

8. The bone plate of claim 1, wherein the interior surface defines a recess surface within the recess, and wherein at least a portion of the recess surface that contains the apex defines a segment of a cylinder.

9. The bone plate of claim 8, wherein the at least a portion of the recess surface is a first portion, and the recess surface further defines a second portion that extends from the first portion toward a central region of the hole, wherein the second portion defines opposite surfaces that are oriented parallel with each other.

10. The bone plate of claim 1, wherein:
the first column defines a first column length measured between the first and second sides of the first column,
the second column defines a second column length measured between the first side of the second column and a second side of the second column opposite the first side thereof, and
the third column defines a third column length measured between the second side of the third column and a first side of the third columns opposite the second side thereof, wherein the second and third column lengths are equivalent and are greater than the first column length.

11. The bone plate of claim 1, wherein the recess circumferentially interrupts an entire thread-form of the at least one of the plate threads.

12. The bone plate of claim 11, wherein the recess circumferentially interrupts entire thread-forms of some and up to all of the plate threads.

13. The bone plate of claim 1, wherein the bone plate is elongate along a longitudinal axis, the bone plate further comprising at least one second hole configured similarly to the at least one hole, wherein the longitudinal axis intersects the apices of the recesses of the at least one hole and the at least one second hole.

14. The bone plate of claim 1, wherein the plate threads extend in an uninterrupted fashion across the first, second, and third columns and the first and second corners.

15. A bone fixation system, comprising:
a bone plate that defines an outer surface, a bone-facing surface opposite the outer surface, and an interior surface that defines a hole extending from the outer surface to the bone-facing surface along a central hole axis, wherein the interior surface further defines:
plate threads extending between the outer surface and the bone-facing surface;
first, second, and third columns sequentially located about the central hole axis;
a first corner extending tangentially from a first side of the second column to a second side of the first column;
a second corner extending tangentially from a second side of the third column to a first side of the first column, wherein the first corner and the second corner are substantially equidistantly spaced from the central hole axis at a first distance measured along a radial direction perpendicular to the central hole axis, and the plate threads extend across the first, second, and third columns and across the first corner and the second corner; and
a recess located between the second and third columns and facing the first column, wherein an apex of the recess is spaced from the central hole axis at a second distance that is greater than the first distance, such that the recess circumferentially interrupts at least a portion of a thread-form of at least some of the plate threads; and
a bone screw having a head and a shaft that extends from the head in a distal direction, wherein the shaft has external threads configured to engage underlying bone, and the head is configured to engage any of the first, second, and third columns in a manner affixing the bone plate to the underlying bone.

16. The bone fixation system of claim 15, wherein the head of the bone screw defines exterior threads configured to threadedly engage the plate threads in a manner locking the head to the interior surface.

17. The bone fixation system of claim 15, wherein an exterior surface of the head of the bone screw is substantially smooth and is configured to contact at least a portion of a recess surface along the recess in a manner causing the bone plate to translate relative to underlying bone along a direction perpendicular to the underlying bone.

18. A bone fixation system, comprising:
a bone plate that defines an outer surface, a bone-facing surface opposite the outer surface, and an interior surface that defines a hole extending from the outer surface to the bone-facing surface along a central hole axis, wherein the interior surface further defines:
plate threads extending between the outer surface and the bone-facing surface;
first, second, and third columns sequentially located about the central hole axis;
a first corner extending tangentially from a first side of the second column to a second side of the first column;
a second corner extending tangentially from a second side of the third column to a first side of the first column, wherein the first corner and the second corner are substantially equidistantly spaced from the central hole axis at a first distance measured along a radial direction perpendicular to the central hole axis, and the plate threads extend across the first, second, and third columns and across the first corner and the second corner; and
a recess located between the second and third columns and facing the first column, wherein an apex of the recess is spaced from the central hole axis at a second distance that is greater than the first distance, such that the recess circumferentially interrupts at least a portion of a thread-form of at least one of the plate threads, and wherein the at least one of the plate threads extends circumferentially in uninterrupted fashion along the interior surface from a first side of the recess to a second side of the recess; and an instrument having a distal mounting portion, wherein the distal mounting portion includes a first formation configured to mate with the hole, and a protrusion extending outwardly from the first formation, wherein the protrusion and the recess define complimentary geometries, such that the protrusion is configured to mate with the recess in a manner securing the first formation with the hole.

19. The bone fixation system of claim 18, wherein the instrument defines a channel extending from a proximal end of the instrument to a distal end of the instrument, wherein a central axis of the channel is configured to be co-extensive with the central hole axis when the protrusion is mated with the recess.

20. The bone fixation system of claim 19, wherein the apex of the recess extends along a first apex trajectory that is parallel with the central hole axis, and the protrusion defines an apex that extends along a second apex trajectory that is parallel with the central axis of the channel, wherein the apex of the protrusion is configured to nest with the apex of the recess.

21. The bone fixation system of claim 20, further comprising a tool configured to extend through the channel and engage underlying bone.

* * * * *